United States Patent
Dematteis et al.

(10) Patent No.: US 6,916,287 B2
(45) Date of Patent: Jul. 12, 2005

(54) MOUTHPIECE INTENDED FOR A DEVICE USED TO ASSESS THE SENSITIVITY OF THE PHARYNX AND A DEVICE COMPRISING SAME

(75) Inventors: Maurice Dematteis, Meylan (FR); Jean-Louis Pepin, Grenoble (FR); Patrick Levy, Grenoble (FR)

(73) Assignee: Universite Joseph Fourier, Grenoble (FR)

( * ) Notice: Subject to any disclaimer, the term of this patent is extended or adjusted under 35 U.S.C. 154(b) by 0 days.

(21) Appl. No.: 10/476,855
(22) PCT Filed: May 13, 2002
(86) PCT No.: PCT/FR02/01595
§ 371 (c)(1),
(2), (4) Date: Dec. 24, 2003
(87) PCT Pub. No.: WO02/091916
PCT Pub. Date: Nov. 21, 2002

(65) Prior Publication Data
US 2004/0138585 A1 Jul. 15, 2004

(30) Foreign Application Priority Data
May 15, 2001 (FR) .......................................... 01 06389

(51) Int. Cl.[7] .............................................. A61B 1/00
(52) U.S. Cl. ..................................... 600/184; 600/237
(58) Field of Search ................................ 600/184, 185, 600/190, 201, 202, 208, 235, 237, 238, 560, 538, 590

(56) References Cited

U.S. PATENT DOCUMENTS

| 1,657,148 A | * | 1/1928 | Catlin .......................... 600/237 |
| 2,756,742 A | | 7/1956 | Barton |
| 3,976,054 A | | 8/1976 | Evans |
| 4,640,273 A | * | 2/1987 | Greene et al. ............... 128/861 |
| 6,517,549 B1 | * | 2/2003 | Dennis ........................ 606/108 |

FOREIGN PATENT DOCUMENTS

WO  WO 96/11627  4/1996

OTHER PUBLICATIONS

Aviv, "Clinical Assessment of Pharyngolaryngeal Sensitivity", The American Journal of Medicine, vol. 108(4A), Mar. 6, 2000, pp 68S–72S.

* cited by examiner

Primary Examiner—Beverly M. Flanagan
(74) Attorney, Agent, or Firm—Oliff & Berridge, PLC

(57) ABSTRACT

To assess the sensitivity of a subject's pharynx, an open mouthpiece (1) fitted with a thin guide tube (2), having an articulated end (4), is inserted into the subject's mouth. A pipe (9) is inserted into the guide tube, under visual observation through the mouthpiece, until it touches the subject's palate. The position on a measurement scale (11) provided on the pipe facing a second end of the guide tube is noted, and the pipe is withdrawn over a preset distance, for example 1 cm, and fixed in this position onto the guide tube. A variable gas flow is injected into the pipe and reaches the pharyngeal mucous situated facing the pipe. The sensitivity of the subject's pharynx, measured by the threshold of sense perception, is determined by the lowest flow value perceived by the subject.

11 Claims, 2 Drawing Sheets

MOUTHPIECE INTENDED FOR A DEVICE USED TO ASSESS THE SENSITIVITY OF THE PHARYNX AND A DEVICE COMPRISING SAME

BACKGROUND OF THE INVENTION

The invention relates to a mouthpiece intended for a device designed for assessing the sensitivity of the pharynx, and a device comprising same.

STATE OF THE TECHNIQUE

Few means exist at present to evaluate the sensitivity of the pharynx. However this evaluation is desirable in a certain number of pathologies involving a malfunctioning of the pharynx, such as sleep apnea. Processes based on mechanical or electrical stimulation of the pharynx are accompanied by undesirable effects, such as inducing a nauseous reflex, which limits the use thereof on a certain number of subjects.

The document WO-A-9,611,627 describes a device using stimulation of the pharynx by a sequence of pulsed air jets of pre-determined duration, for example 50 ms, and of variable pressure, for example between 0 and 10 mm of mercury in steps of $7.5 \times 10^{-2}$ mm of mercury. The pulsed air jets are injected into the zone to be tested via a flexible tube of small diameter fixed to a fibroscope which is inserted into the nose of the patient to be examined, like those commonly used for observation of the pharynx. The pipe conveying the air may be integrated in the fibroscope. The patient's response to the stimulus constituted by a pulsed air jet can correspond either to an indication given by the patient or to observation of a reflex such as closing of the vocal chords observed by means of a fibroscope. Such a device is complex and costly. It does in fact require a sophisticated technical set-up and specialised skills from the user, which limits the number of subjects able to be examined.

OBJECT OF THE INVENTION

The object of the invention is to overcome the drawbacks of known systems and to provide simple, inexpensive means of evaluating the sensitivity of the pharynx, limiting the undesirable effects on the patient.

According to the invention, this object is achieved by a mouthpiece to be used for evaluating the sensitivity of the pharynx that comprises an open mouthpiece having internal dimensions enabling visual inspection of the pharynx, a thin guide tube fixed along an internal wall of the mouthpiece and comprising a first articulated end salient from a first end of the mouthpiece, a pipe designed to be connected via a first end to a compressed gas source and inserted via a second end inside the guide tube, and means for fixing the pipe in the guide tube in a pre-determined position.

The invention also relates to a device for evaluating the sensitivity of the pharynx, comprising a compressed gas source, means for blowing gas in the direction of the pharynx, a mouthpiece according to the invention and means for measuring the flow rate of a gas injected into a first end of the pipe.

A process for using a device according to the invention for evaluating the sensitivity of the pharynx comprises insertion of the first end of the mouthpiece into the subject's mouth, insertion of the second end of the pipe into the guide tube, checked visually through the mouthpiece, until it touches the subject's palate, withdrawal of the pipe over a preset distance measured by graduations of the pipe, connection of the first end of the pipe to the compressed air source, injection of a variable air flow of preset flowrate into the pipe, the sensitivity of the pharynx being determined according to the flow values for which the subject is able to feel the air flow.

BRIEF DESCRIPTION OF THE DRAWINGS

Other advantages and features will become more clearly apparent from the following description of particular embodiments of the invention given as non-restrictive examples only and represented in the accompanying drawings in which.

DESCRIPTION OF PARTICULAR EMBODIMENTS

Figure 1:
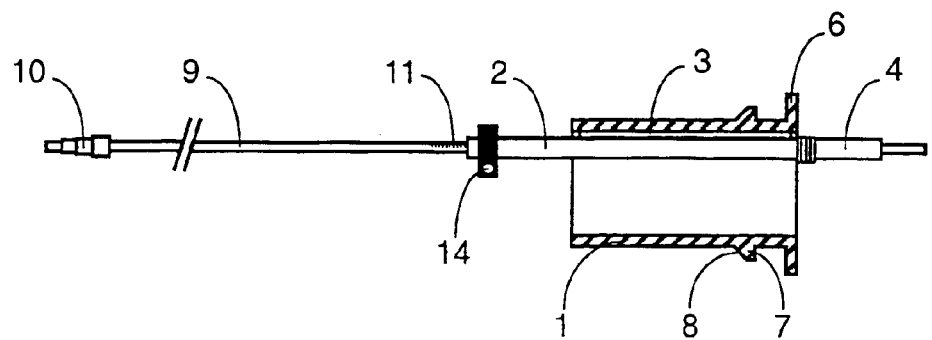
FIG. 1 represents, in cross-section, a particular embodiment of a mouthpiece according to the invention.
Figure 2:
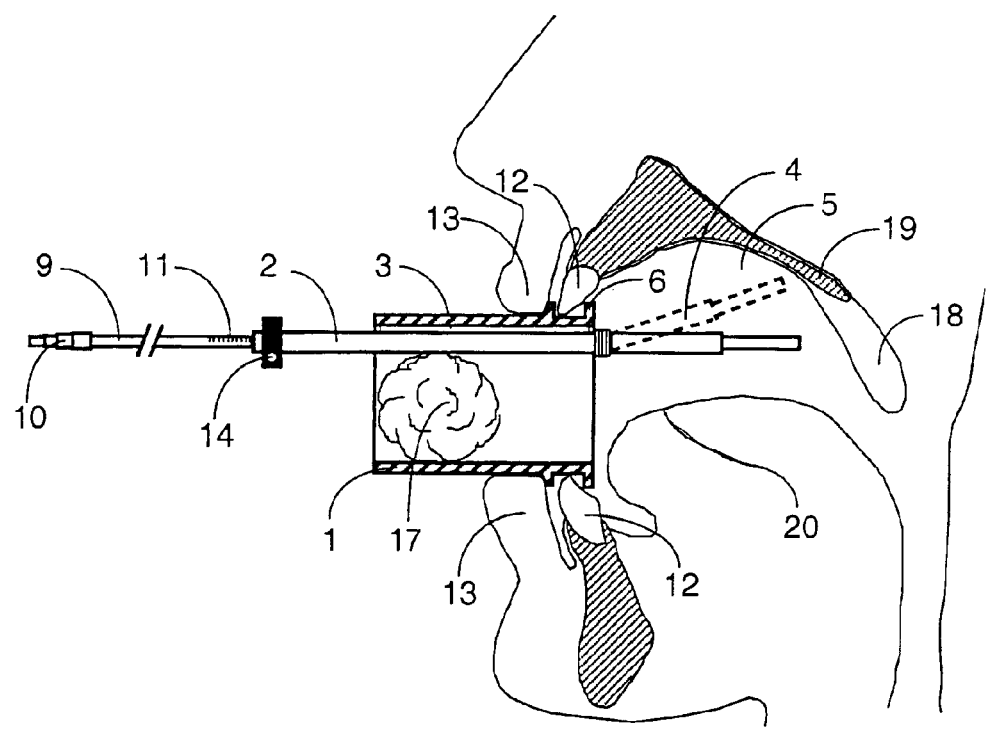
FIG. 2 represents the mouthpiece according to FIG. 1 in position in a patient's mouth.

The mouthpiece represented in FIGS. 1 and 2 comprises an open mouthpiece 1 forming the body of the mouthpiece and preferably formed by a cylinder open at both ends, a few centimeters in diameter and a few centimeters in length. As an example, the cylinder can be 2 to 3 cm in diameter and 4 cm in length. It can be narrower to enable evaluation of the sensitivity of the pharynx of subjects, like children, whose mouth opening is narrow. Its length can be reduced to make it easier to keep it in the subject's mouth.

A thin guide tube 2 is fixed, for example by glue 3, along an internal wall of the mouthpiece 1. The guide tube 2 is preferably formed by a blow-pipe, i.e. a small tube or straw, made of plastic material, generally used to suck a liquid. It has a diameter of a few millimeters, for example 4 to 5 mm, and extends a few centimeters, for example 3 cm, beyond each end of the mouthpiece. It is moreover articulated at a first end 4 designed to be inserted into the subject's buccal cavity 5. This articulation enables the end 4 of the guide tube 2 and the pipe 9 described above to be positioned facing the membranous palate 18, between the bony palate 19 and the tongue 20, whatever the morphology of the oral cavity of the subject examined. In FIG. 2, a second position of the end 4 is illustrated in a broken line.

The mouthpiece 1 comprises an external holding rim 6 at a first end designed to be inserted into a subject's mouth. A rib 7, substantially parallel to the holding rim 6, can be provided to make it easier for the subject to keep the mouthpiece in his mouth. The rib 7 preferably comprises an inclined face 8 on the side opposite the holding rim 6.

The mouthpiece also comprises a pipe 9 designed to be connected via a first end to a compressed gas source and inserted via a second end into the guide tube 2. The diameter of the pipe 9 is slightly smaller than that of the guide tube 2 so as to be able to be easily inserted into the latter. In a preferred embodiment, the diameter of the pipe 9 is about 2 mm. The pipe 9 can for example be formed by an oxygen probe of conventional type made of flexible plastic material, comprising a connecting element 10 at its first end for connection to the compressed gas source.

The pipe 9 comprises a measurement scale 11 designed to cooperate with the second end of the guide tube 2, opposite its articulated first end 4, and located outside the subject's buccal cavity 5 during use of the mouthpiece.

To evaluate the sensitivity of a subject's pharynx, the mouthpiece 1 equipped with the guide tube 2, the articulated end 4 whereof is directed in a suitable manner, is inserted into the subject's mouth via its first end comprising the holding rim 6. As represented in FIG. 2, the teeth 12 of the subject's upper and lower maxillaries are placed behind the holding rim 6, between the holding rim and the rib 7, thus securing the mouthpiece 1 in the subject's mouth. The subject's lips 13 then take the same shape as that of the mouthpiece 1 and rest notably on the inclined face 8 of the rib 7. Only a small part of the mouthpiece 1 is then in the subject's mouth, most of the mouthpiece 1, from the rib 7 to the second end of the mouthpiece 1, opposite the holding rim 6, extending outside.

The internal dimensions of the mouthpiece are such as to enable visual inspection of the pharynx, in spite of the presence of the guide tube 2. The second end of the pipe 9 is inserted into the guide tube 2, under visual observation through the mouthpiece 1, until it touches the subject's palate. The position on the measurement scale facing the second end of the guide tube is noted, and the pipe is then withdrawn over a preset distance, for example 1 cm. There is then no longer any contact between the end of the pipe and the palate, but the distance between this end and the palate is still the same whatever the morphology of the palate of the subject examined. A clamp 14, or in the absence thereof, sticky tape, is then used to fix the pipe 9 in this position with respect to the guide tube 2.

Figure 3:
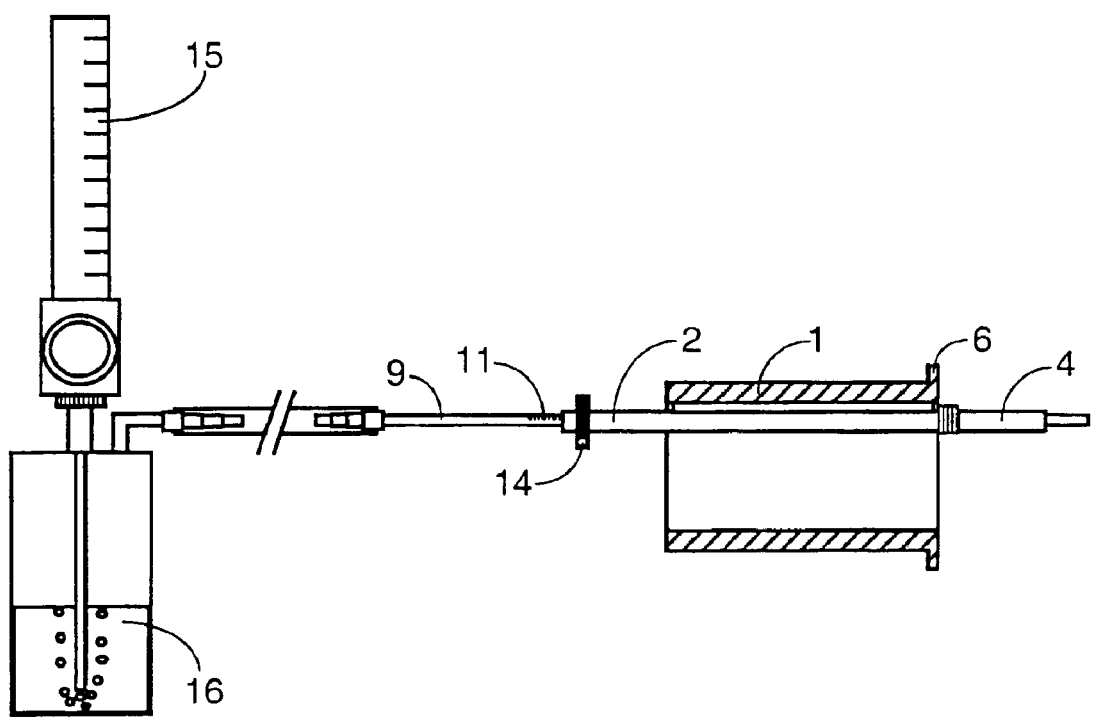
FIG. 3 represents a particular embodiment of a device according to the invention.

The pipe 9 is connected, possibly by means of a connection of larger diameter and a wall socket, to a compressed gas source, preferably to a compressed air bottle or an oxygen bottle. A flowmeter 15 (FIG. 3) enables the gas flow injected into the pipe 9 to be adjusted and measured accurately. A variable gas flow of preset flow rate is injected into the pipe 9 and reaches the pharyngeal mucous of the palate situated facing the pipe 9. To give the subject being examined a first indication of the sensation he should feel, a high flow, for example 2 L/min, is administered and is then progressively reduced in steps, asking the subject at each step if he still perceives the sensation. He indicates, by means of the means of indicating agreed on before the examination, whether he perceives the gas flow or not. The lowest flow still perceived corresponds to the threshold of sense perception. To validate the measurement, the procedure is repeated at least two more times and the different values obtained are then averaged. The perception threshold is then measured by administering increasing flows per step, starting from a nil flow. At each step the subject is asked if he perceives the flow. The lowest value of the gas flow perceived corresponds to the threshold of sense perception. Measurement is repeated at least twice and the different values obtained are then averaged. Asking at each step whether the subject perceives a sensation may potentially influence the answer. Another way of proceeding is therefore to ask the subject to indicate by a physical gesture, or by any other means, when the pharyngeal sensation disappears or appears. During the experiment, the subject is requested to close his eyes and headphones may be fitted on his ears to facilitate concentration on perception of the flow at the level of the pharyngeal mucous. The headphones also prevent the subject's responses from being influenced by the sound of modifications of the gas flow. Finally, in the course of the examination, the subject has to breathe through his nose to prevent any interference between the gas flow administered on the mucous and the air breathed in. For this purpose, the mouthpiece may be blocked up at its second end, in particular by means of a ball of cotton-wool 17.

This device is very simple and inexpensive. The graduations of the pipe 9 suffice, in combination with a temporary prior contact of the second end of the pipe with the palate, under visual observation, to ensure a standard positioning for all subjects. The articulation of the first end of the guide tube 2 moreover enables the device to be adapted to the morphology of the palate of a large number of subjects. Only the rate of the gas flow is taken into account, neither its pressure nor the injection time having to be taken into account. Such a device can easily be used by any doctor having a compressed air or oxygen source at his disposal.

To avoid drying of the pharyngeal mucous in the course of the examination, the device can comprise a humidifier 16 (FIG. 3), fitted between the gas source and the inlet of the pipe 9, which humidifies the gas injected into the pipe.

The humidifier 16 can comprise water, which can be heated to a variable, preset temperature. It is then possible to evaluate the sensitivity of the pharyngeal mucous to temperature as well.

The method can be made more sensitive by using a local anaesthetic, for example xylocaine, sprayed onto the pharyngeal mucous situated facing the pipe 9, under visual observation through the mouthpiece 1 or directly after the device has been removed. The sensitivity is then re-evaluated after a minimum time delay enabling the anaesthetic to produce its effect, for example 5 minutes. Then other sprayings of the local anaesthetic can be administered onto the pharyngeal mucous using the same procedure in order to define an effect-to-dose relationship.

Due to the heterogeneity of the sensitive innervation of the pharyngeal mucous, the sensitivity can be evaluated using the same procedure as that described above on zones other than that of the palate, such as for example the pillar of fances, the rear wall of the pharynx or the nasopharynx.

Due to the heterogeneity of the chemical receptors (chemoreceptors) of the pharyngeal mucous, the gas flow can consist of a flow of air, oxygen or carbon dioxide in order to evaluate the respective part played by the different types of receptors in sense perception of the pharyngeal mucous and their involvement in pathologies arising from malfunctioning of this perception.

In order to evaluate the different parts of the dilating reflex arc of the pharynx (afferent sensitive part and efferent motor part), it can be envisaged to combine sensitive evaluation, as has been described above, with evaluation of the motor response, such as appreciation of the electromyographic activity of a pharynx dilating muscle, for example the genioglossus muscle, in particular in response to a negative pressure applied to the upper respiratory tract.

In order to eliminate the subjective nature of the subject's responses, or to avoid non-understanding of the instructions or to overcome a lack of co-operation, it can be envisaged to combine evaluation of sensitivity with recording of somesthetic evoked potentials. A sufficiently high air flow to trigger a sensitive stimulation, for example 2 L/min, then has to be fixed, and this gas flow be administered in brief and intermittent manner at a given frequency and for a sufficient time for it to evoke an electro-encephalographic cortical response (evoked potential) that is able to be averaged.

What is claimed is:

1. A mouthpiece intended for a device designed for evaluating the sensitivity of the pharynx, characterized in that it comprises an open mouthpiece having internal dimensions enabling visual inspection of the pharynx, a thin guide tube fixed along an internal wall of the mouthpiece and comprising a first articulated end salient from a first end of the mouthpiece, a pipe designed to be connected via a first end to a compressed gas source and inserted via a second end inside the guide tube, and means (14) for fixing the pipe in the guide tube in a pre-determined position.

2. Mouthpiece according to claim 1, wherein the pipe comprises a measurement scale.

3. Mouthpiece according to claim 1, wherein the mouthpiece is cylindrical.

4. Mouthpiece according to claim 1, wherein the mouthpiece comprises an external holding rim at its first end.

5. Mouthpiece according to claim 4, wherein the mouthpiece comprises a holding rib.

6. Device for evaluating the sensitivity of the pharynx, comprising a compressed gas source and means for blowing gas in the direction of the pharynx, comprising a mouthpiece according to claim 1 and means for measuring the flow rate of a gas injected into the first end of the pipe.

7. Device according to claim 6, wherein the gas is air.

8. Device according to claim 6, wherein the gas is oxygen.

9. Device according to claim 6, wherein the gas is carbon dioxide.

10. Device according to claim 6, characterized in that it comprises humidifying means to humidify the air injected into the pipe.

11. Device according to claim 10, wherein the humidifying means comprise water heated to a variable preset temperature.

* * * * *